(12) United States Patent
Tucek et al.

(10) Patent No.: US 10,857,378 B2
(45) Date of Patent: Dec. 8, 2020

(54) HAND-HELD LASER TREATMENT DEVICE WITH AUTOMATIC SWEEP AND ADJUSTABLE SWEEP AMPLITUDE

(71) Applicants: Kevin B Tucek, Melbourne, FL (US); Steven C Shanks, Melbourne, FL (US)

(72) Inventors: Kevin B Tucek, Melbourne, FL (US); Steven C Shanks, Melbourne, FL (US)

(73) Assignee: Erchonia Corporation, LLC, Melbourne, FL (US)

( * ) Notice: Subject to any disclaimer, the term of this patent is extended or adjusted under 35 U.S.C. 154(b) by 329 days.

(21) Appl. No.: 15/998,778

(22) Filed: Aug. 16, 2018

(65) Prior Publication Data

US 2020/0054892 A1    Feb. 20, 2020

(51) Int. Cl.
*A61N 5/06* (2006.01)
*A61N 5/067* (2006.01)
*A61B 18/20* (2006.01)

(52) U.S. Cl.
CPC .. *A61N 5/0616* (2013.01); *A61B 2018/20355* (2017.05); *A61N 2005/067* (2013.01); *A61N 2005/0626* (2013.01); *A61N 2005/0644* (2013.01); *A61N 2005/0652* (2013.01); *A61N 2005/0659* (2013.01); *A61N 2005/0661* (2013.01); *A61N 2005/0663* (2013.01)

(58) Field of Classification Search
CPC .............. A61B 2018/20355; A61N 2005/0644
See application file for complete search history.

(56) References Cited

U.S. PATENT DOCUMENTS

| | | | |
|---|---|---|---|
| 6,746,473 B2 | 6/2004 | Shanks | |
| 7,118,588 B2 | 10/2006 | Tucek | |
| 7,947,067 B2 | 5/2011 | Tucek | |
| 2006/0224218 A1* | 10/2006 | Tucek | A61N 5/0616 607/89 |
| 2013/0077643 A1* | 3/2013 | Spears | G01B 11/00 372/24 |

* cited by examiner

*Primary Examiner* — Michael W Kahelin
(74) *Attorney, Agent, or Firm* — Etherton Law Group, LLC (57) ABSTRACT

A hand-held laser treatment device automatically sweeps a line of laser energy across a treatment area of a patient without moving the device. Laser energy sources reside in a scan head housing, which is rotatably connected to a body housing at a housing mount. A motorized scanning mechanism in the body housing drives a pushrod connected that is to the scan head to cause the scan head to reciprocate about the housing mount axis, moving an emitted line of laser energy up and down. The scanning mechanism comprises a rotational motor, a pushrod drive cam, a guide cam and an amplitude adjustor, all coaxially aligned along a motor axis. Interposed between the pushrod drive cam and the guide cam are the pushrod and a guide bearing aligned along an axis parallel to the motor axis. The degree of sweep is adjustable to change the size of the area treated.

15 Claims, 7 Drawing Sheets

HAND-HELD LASER TREATMENT DEVICE WITH AUTOMATIC SWEEP AND ADJUSTABLE SWEEP AMPLITUDE

FIELD OF INVENTION

This invention relates generally to low-level laser devices for treating patients. More particularly, this invention relates to a laser treatment device that automatically sweeps a laser line across a desired treatment area in which the amplitude of the sweep is adjustable.

BACKGROUND

Low-level laser therapy ("LLLT") is used in the treatment of a broad range of conditions. LLLT improves wound healing, reduces edema, and relieves pain of various etiologies, including successful application to wound and surgical sites to reduce inflammation and pain. LLLT is also used in the treatment and repair of injured muscles and tendons. LLLT utilizes low level laser energy, wherein the treatment has a dose rate that causes nu immediate detectable temperature rise of the treated tissue and no macroscopically visible changes in tissue structure. Consequently, the treated and surrounding tissue is not heated or damaged, and the patient feels no sensation during treatment.

Low-level laser therapy devices are conventionally hand-held devices that emit laser energy. In popular commercial devices, such as those described in U.S. Pat. No. 6,746,473, the emitted laser energy strikes the surface as a line, as opposed to a dot. In order to cover the whole treatment area, the device operator holds the device and moves his hand or arm in a back-and-forth motion to sweep the line of emitted energy across a targeted body part, thereby treating a certain area of the patient's body. This treatment method requires that the operator move his hand or arm repeatedly, which can become tiring during a long treatment or if multiple treatments are applied in series. Due to inconsistency inherent in human motion, the amplitude of each sweep varies from sweep-to-sweep, causing uncertainty in the dose of laser energy applied to the target body part. Having to hold the laser device during treatment also prevents the operator from performing other functions during treatment.

In other low-level laser therapy devices known in the art such as U.S. Pat. Nos. 7,118,588 and 7,947,067, a scanning mechanism deflects or reflects laser energy after it is emitted from the laser energy source to form various shapes which are projected onto the patient. As with the laser devices described above, these laser energy sources are stationary relative to the housing of the device. Therefore, to cover the whole treatment area, the entire device must be moved in a back-and-forth motion to sweep the emitted energy across the targeted treatment area. It would be desirable to provide a hand-held laser device that enables a treatment area to be scanned without the operator moving the entire device with his hand or arm.

Other low-level laser therapy devices known in the art are stationary plates of stationary laser emission sources that treat an area of a patient's body directly and simultaneously. One disadvantage of stationary laser energy sources is that to change the area being treated, the treatment must be stopped while the patient or the device is moved to adjust the treated area. Another disadvantage is that the size of the treatment area is limited to the size of the plate.

It would be desirable to provide a laser device that enables an operator to scan a treatment area without moving the laser with his hand or arm. It would be desirable to provide a laser device that enables an operator to change the amplitude of the sweep, thereby adjusting the area of treatment. It would be desirable to provide a laser device that enables an operator to change the treatment area without having to stop the treatment to reposition the patient or the device.

SUMMARY OF THE INVENTION

This invention is a hand-held laser treatment device that automatically sweeps laser energy across a desired area of a patient without moving the device. Laser energy sources reside in a scan head housing, which is rotatably connected to a body housing at a housing mount. A motorized scanning mechanism in the body housing drives a pushrod that is connected that is to the scan head to cause the scan head to reciprocate about the housing mount axis, moving an emitted line of laser energy up and down. The scanning mechanism comprises a rotational motor, a pushrod drive cam, a guide cam and an amplitude adjustor, all coaxially aligned along a motor axis. Interposed between the pushrod drive cam and the guide cam are the pushrod and a guide bearing aligned along a a pushrod axis that is parallel to the motor axis. The degree of sweep is adjustable to change the size of the area treated.

DETAILED DESCRIPTION OF THE INVENTION

This invention is a hand-held laser treatment device that automatically sweeps laser energy across a desired treatment area of a patient without having to move the device. An operator holds the device still and the attached scan head moves back and forth, causing the emitted laser energy to sweep back and forth across the treatment area where the device is aimed. The size of the treatment area can be changed by adjusting the amplitude of the sweep.

Figure 1A:
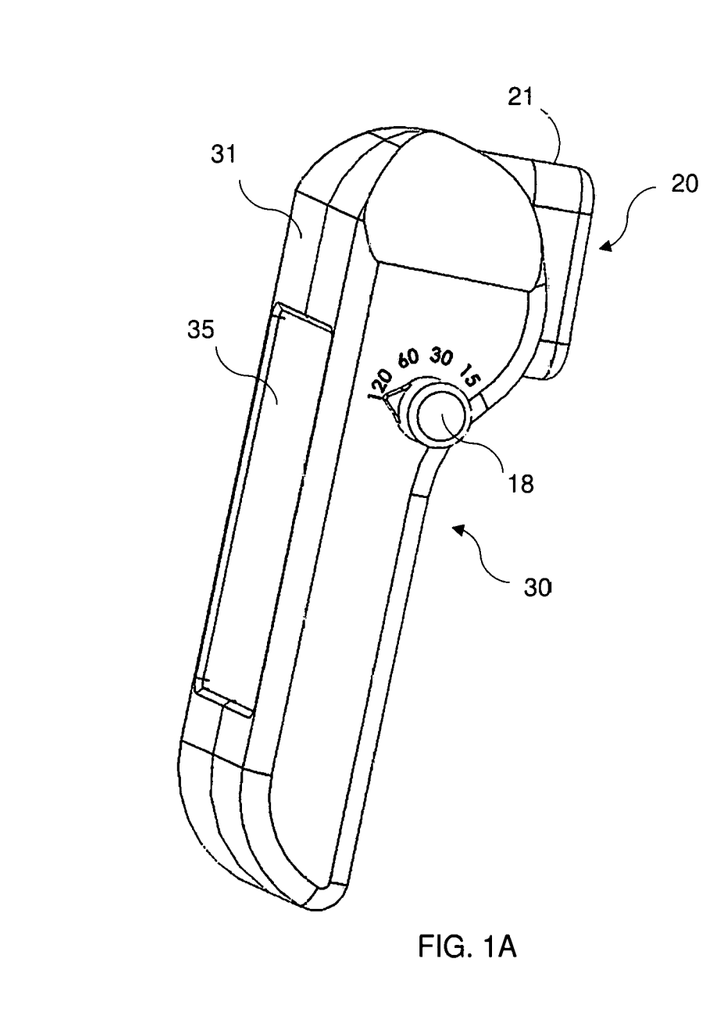
FIG. 1A is a side perspective view of the laser treatment device.

The device comprises a moveable scan head 20 connected to a body 30. See FIGS. 1A and 1B. The scan head 20 is attached to the body 30 at a housing mount 22. Typically the body housing 31 is shaped and sized to fit in an operator's hand. In some embodiments the body housing 31 may be inserted into receiver on a stand or arm, which permits the hand-held scanner to be used in a hands-free mode while scanning the treatment area. The hands-free mode is particularly useful for protocols that require a longer treatment time, and it reduces strain on the operator and frees him to perform other functions during treatment.

Figure 2A:
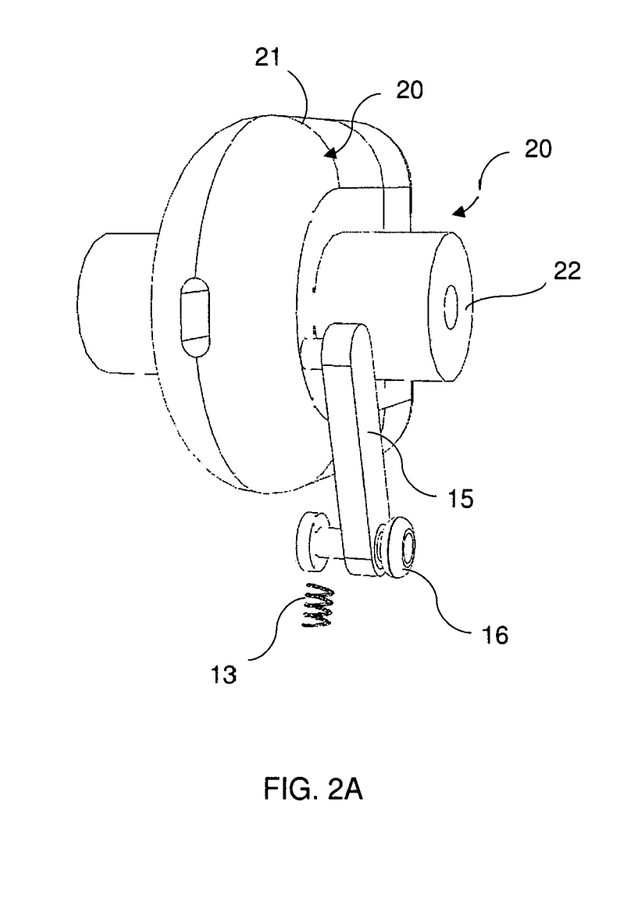
FIG. 2A is a rear perspective view of the scan head and pushrod.
Figure 2B:
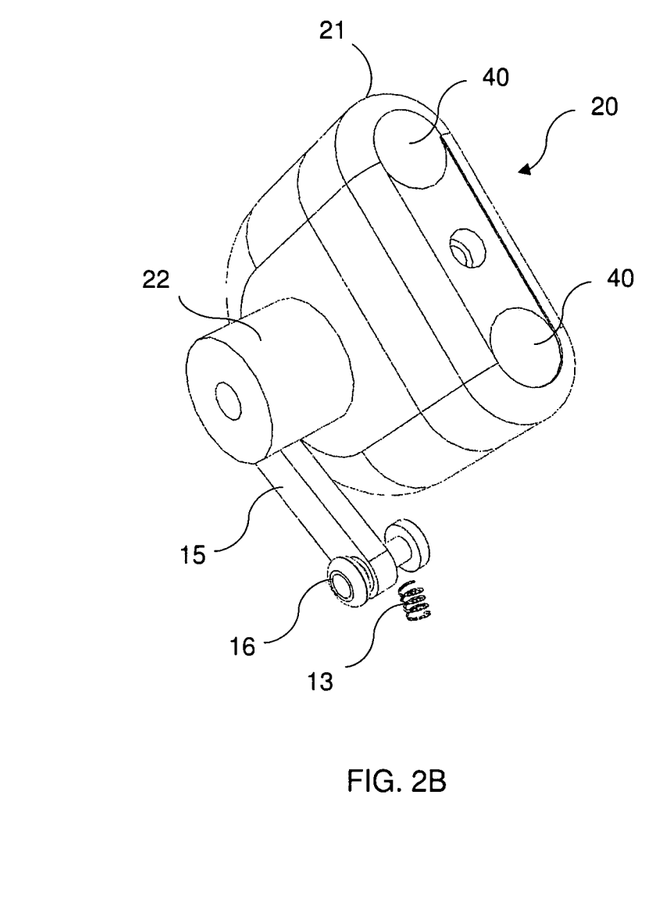
FIG. 2B is a front perspective view of the scan head and pushrod.

One or more laser energy sources 40 is disposed in a scan head housing 21 and a scanning mechanism 11 is disposed within a body housing 31. FIGS. 2A and 2B show the scan head housing 21 configured to receive two laser diodes 40. If more than one diode is used, preferably the diodes are arranged vertically relative to the scan orientation, as shown in the figures herein. In other embodiments the diodes are arranged in other relationships, such as horizontally relative to the scan orientation, diagonally, or in rows or columns in either the vertical or horizontal configuration.

A broad range of emitted wavelengths can be used in low level laser therapy, from ultraviolet to infrared, depending on the desired treatment. The laser energy sources in the preferred embodiment are semiconductor laser diodes that emit light in the red range of the visible spectrum, having a wavelength of about 635 nm. For low-level laser therapy protocols that use ultraviolet or infrared laser energy, it is advantageous to utilize at least one additional laser energy source that emits light in the visible spectrum so that the operator can see the laser light as it impinges the patient's body and the area treated can be easily ascertained. Laser energy sources for low-level laser therapy are typically less than one watt.

The laser energy emitted from the laser energy sources has a spot shape when it impinges the patient's body, depending on how the laser energy is reflected or refracted after it is emitted from the laser energy source. For example, a laser beam of circular cross-section creates a circular beam spot as the laser energy impinges the patient's skin. If the laser energy emitted is in the visible range, a circular spot can be seen on the patient's skin. In the preferred embodiment, the emitted laser energy forms a line of laser energy on the patient's body, which is swept up and down to treat a desired area. See FIG. 3. Line-generating laser devices are known in the art, such as the ones disclosed in the inventor's other patents including U.S. Pat. No. 6,746,473, which is incorporated herein by reference in its entirety. One embodiment includes a collimating lens and a line generating prism disposed in serial relation to the laser energy source to receive and transform the generated beam of laser energy into the line of laser energy. In another embodiment a rod lens transforms the generated beam of laser energy into the line of laser energy. Alternatively, a suitable electrical or mechanical arrangement could be used to shape the laser energy instead of optical elements. The device may utilize as many lasers and shaping elements as necessary to obtain the desired emissions and spot shapes. For example, the device may employ two laser diodes each with a collimating lens, such that two substantially circular spot shapes are achieved. In another embodiment, the device may employ two laser diodes each with optical elements such that two substantially linear spot shapes are achieved. Or, in another example, more than two lasers may be used and optical arrangements aligned such that two or more of the laser beams have substantially similar spot shapes and are co-incident where they impinge the patient's skin. The line-generating components reside in the scan head housing 21.

Figure 1B:
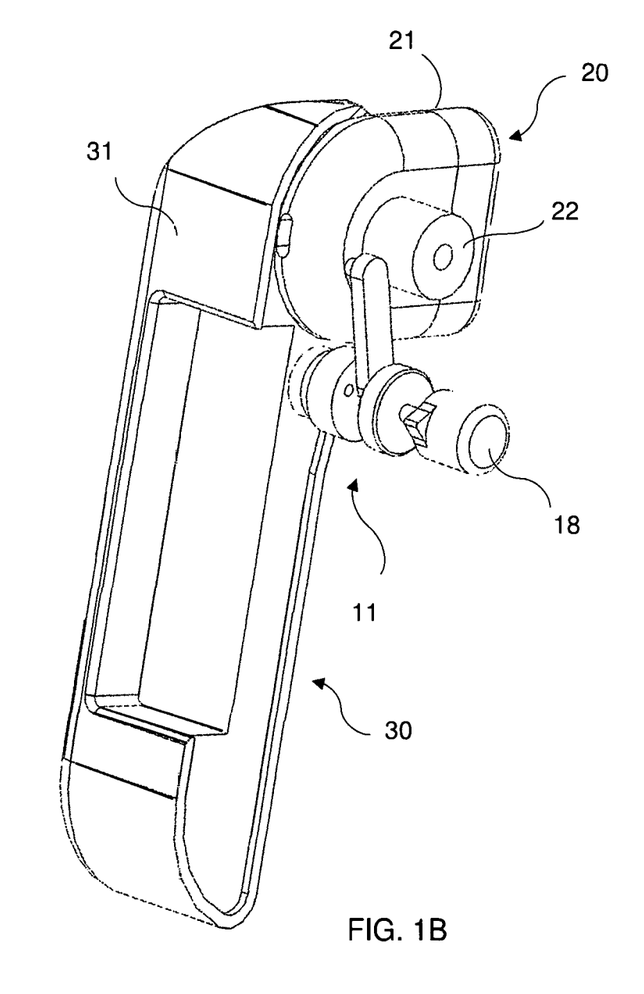
FIG. 1B is a cutaway view of the laser treatment device.
Figure 3:
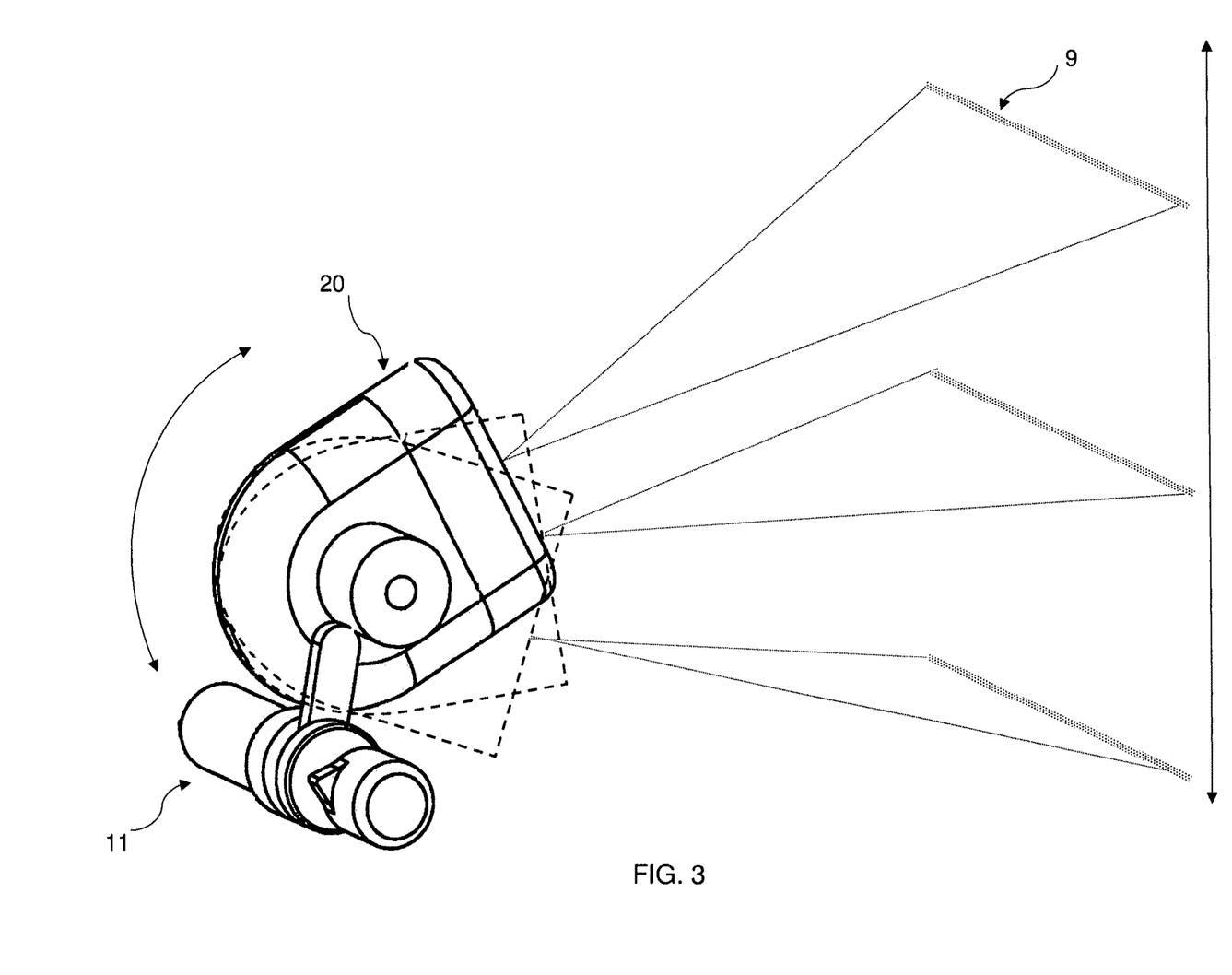
FIG. 3 illustrates the emitted laser energy as the scan head moves up and down.

The scan head 20 and a scanning mechanism 11 cooperate to automatically sweep laser energy across a desired treatment area of a patient without having to move the body of the device. The scanning mechanism 11 is typically disposed in the body housing 31 as shown in FIG. 1B, but is shown without the body housing in FIGS. 3, 5A and 5B for clarity. The scanning mechanism 11 drives a pushrod 15 that is connected to the scan head 20 in a reciprocating motion (also referred to as back and forth, up and down, or side to side), which in turn moves the scan head 20 up and down. FIG. 3 shows three instances of the position of a scan head 20 employing a single laser energy source, but in operation the scan head 20 reciprocates without stopping. The scan speed can be mechanically preset, i.e. the scan motor speed set at a fixed speed that the operator cannot change, or the scan motor speed can be controllable by the operator. A fast scan speed will make the laser light appear to be a rectangle on the surface it impinges because each scan pass will happen so fast that the eye cannot differentiate the passes, similar to the effect of the high frame rate of a motion picture. But, preferably the device scans at a lower speed so that the line is visible at it traverses the surface.

Figure 5A:
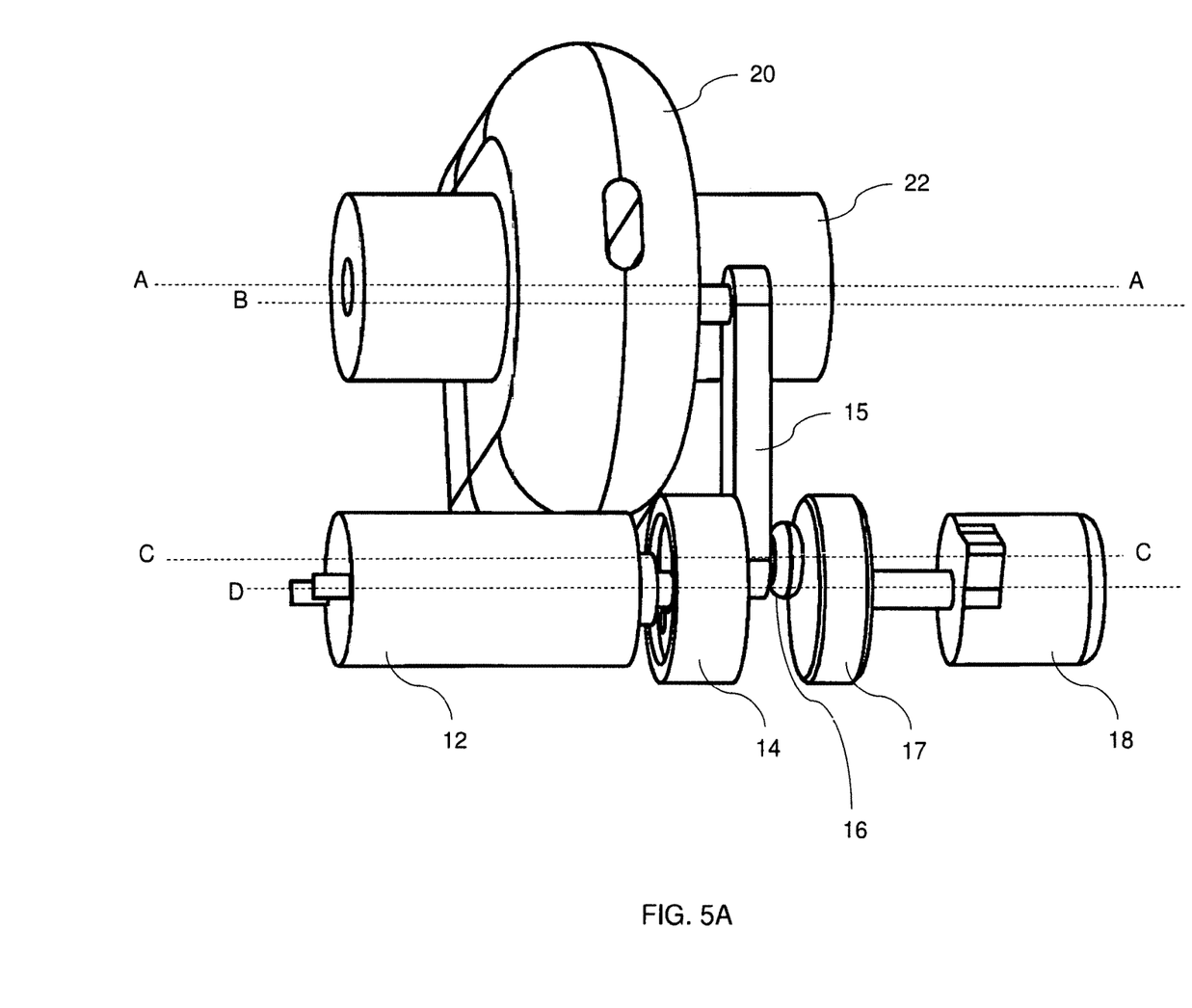
FIG. 5A is a rear perspective view of the scanning mechanism and scan head.
Figure 5B:
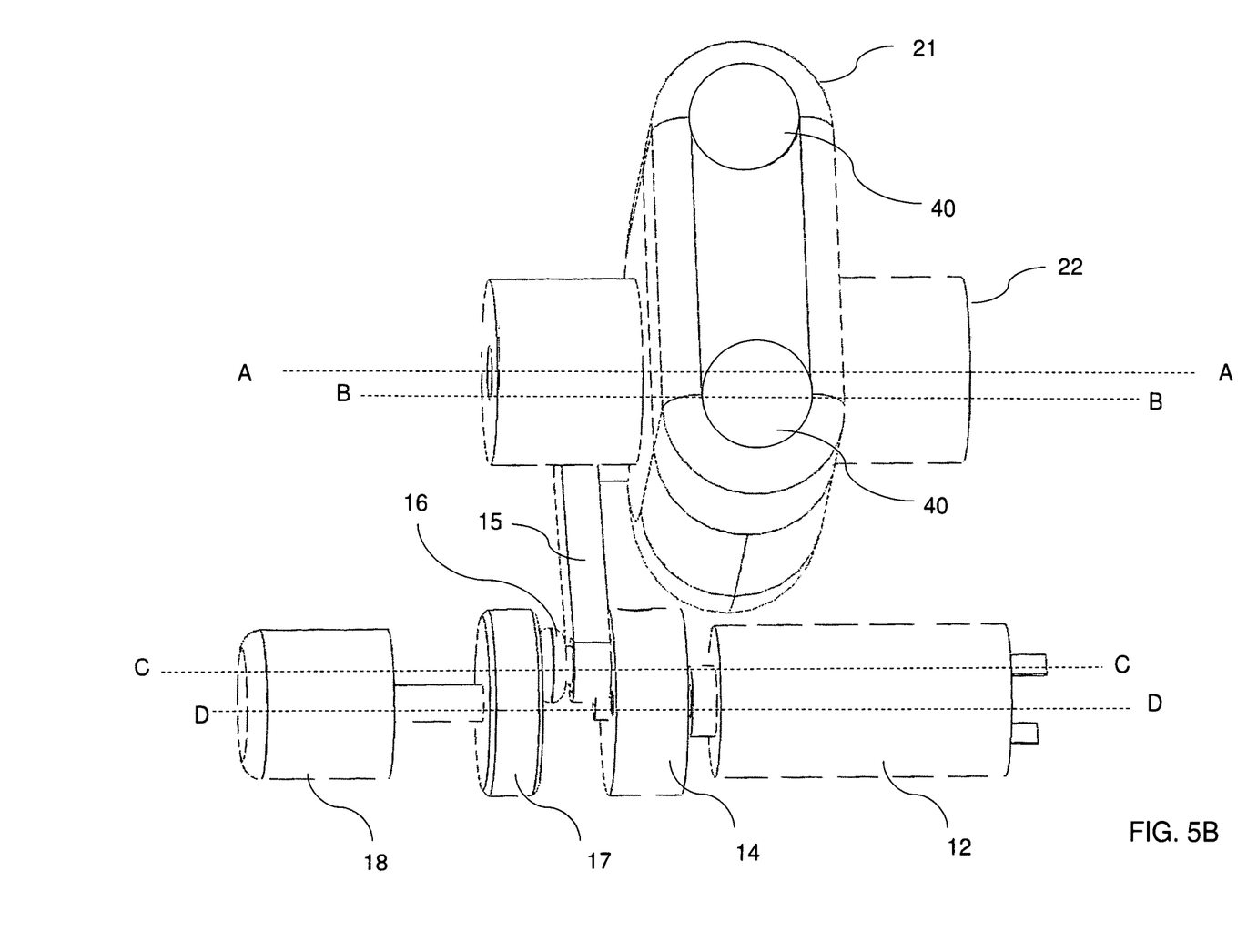
FIG. 5B is a front perspective view of the scanning mechanism and scan head.
Figure 6A:
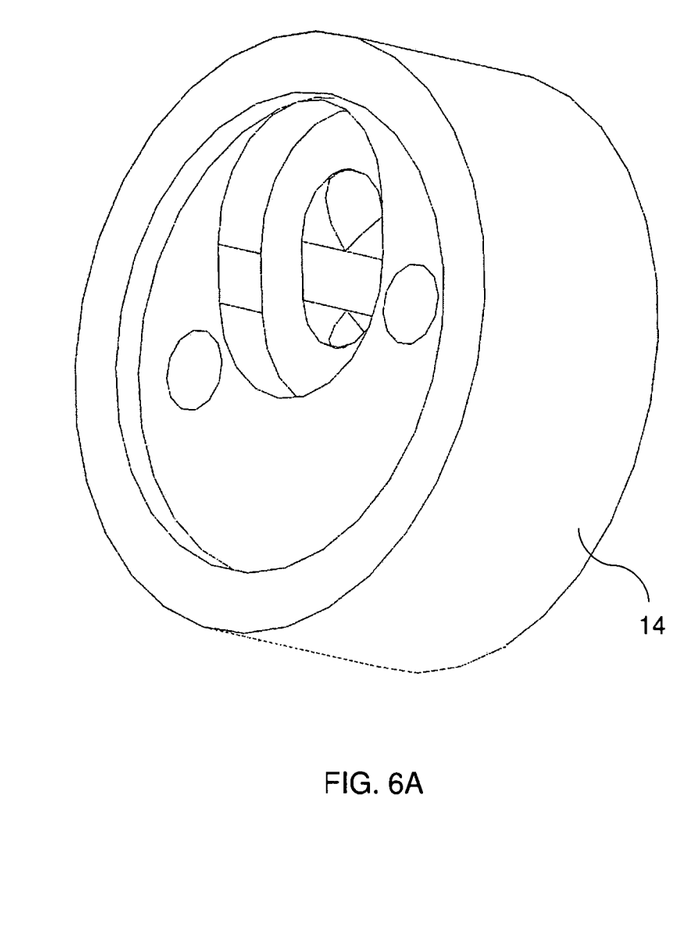
FIG. 6A is a left perspective view of the pushrod drive cam.
Figure 6B:
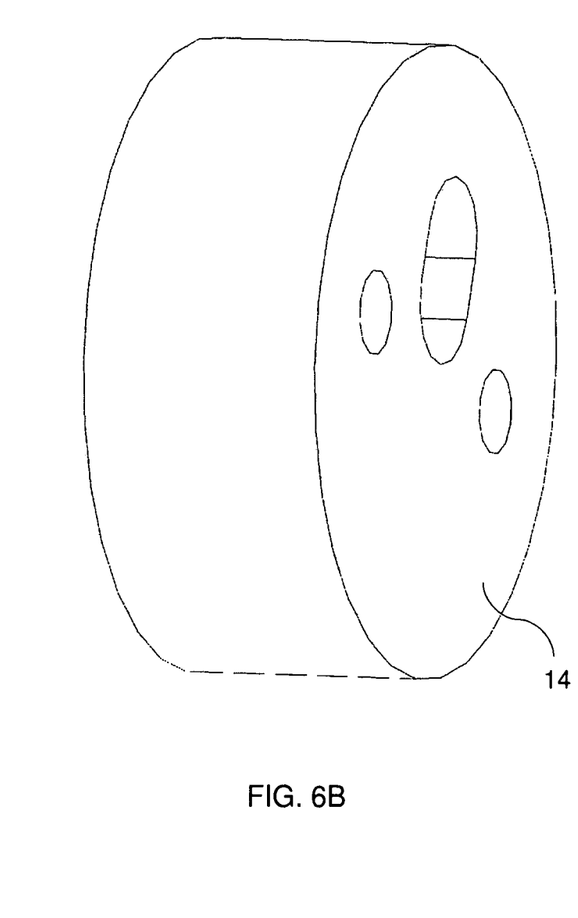
FIG. 6B is a right perspective view of the pushrod drive cam.

In some embodiments, a rocker motor drives a rocker arm to drive the pushrod. In other embodiments, a rotational motor 12 drives a pushrod drive cam 14 to drive the pushrod 15. In a preferred embodiment, as shown in FIGS. 5A and 5B, the scanning mechanism 11 comprises a rotational motor 12, a pushrod drive cam 14, a guide cam 17 and an amplitude adjustor 18, all coaxially aligned along a motor axis D. Interposed between the pushrod drive cam 14 and the guide cam 17 is a pushrod 15 and a guide bearing 16, coaxially aligned along a pushrod axis C that is parallel to the motor axis D. The proximal end of the pushrod 15 is rotatably connected to the pushrod drive cam 14 along axis C. The pushrod 15 floats within the pushrod drive cam 14 and a spring 13 inside the pushrod drive cam 14 urges the pushrod 15 towards the perimeter of the guide cam 17. See FIGS. 2A, 2B, 6A and 6B. The distal end of the pushrod 15 is rotatably connected to the scan head 20 at a point along axis B, which is parallel to the housing mount axis A. Thus, when the motor 12 is on, the scanning mechanism 11 causes the connected pushrod 15 to move the scan head 20 up and down in a reciprocating motion. The scan head 20 rotates relative to the body housing 31 in partial arcs about the housing mount axis A, and sweeps laser energy back and forth across the treatment area.

Figure 4:
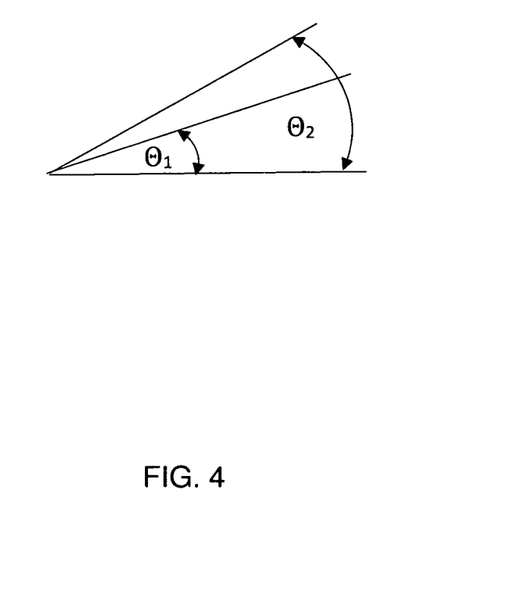
FIG. 4 is a diagram illustrating the amplitude of the sweep.

The sweep amplitude can be adjusted to increase or decrease the amount the scan head rotates above the housing mount, thus increasing or decreasing, respectively, the size of the scanned area. The amplitude, or angle θ, of the sweep may be adjusted by lengthening or shortening the stroke of the pushrod. See FIG. 4. To accomplish this, an adjustor moves the guide bearing 16 along axis C relative to the guide earn 17 aligned along axis D. The face of the guide cam 17 is concave and the guide bearing 16 rides along a circumference on the face of the guide cam 17. As the guide cam 17 is moved closer to the guide bearing 16, the guide bearing 16 is gently forced toward the center of the guide cam 17, shortening the radius of the circumference of travel of the pushrod 15, which translates into a shorter pushrod stroke. The smaller amplitude is illustrated as θ1 in FIG. 4. Conversely, as the guide cam 17 is moved away from the guide bearing 16, the guide bearing 16 is gently permitted to travel toward the perimeter of the guide cam 17, lengthening the radius of the circumference of travel, which translates into a longer pushrod stroke. For comparison, the larger amplitude is indicated illustrated as θ2 in FIG. 4. In one embodiment the adjustor is a knob 18 that mechanically moves the guide cam closer to or farther away from the guide bearing. In other embodiments, the adjustor comprises a motor that can be controlled by a manual switch or by a microcontroller.

Preferably the device is cordless and powered by rechargeable batteries, but it may also be corded and powered by mains. Control circuitry is connected to the laser energy sources and scanning mechanism to control the device, including parameters such as pulse frequency, treatment duration, and rate of reciprocation. A display 35 indicates the control parameters and the status of the device. In some embodiments, the display is a touch screen for changing device parameters. In some embodiments the device is programmable using an onboard software application, a mobile app, or by wireless connection to an online application.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

The invention claimed is:

1. A laser device comprising:
    a. a scan head comprising one or more laser energy sources that are stationary relative to the scan head;
    b. a scanning mechanism connected to the scan head which causes the scan head to move up and down relative to a body housing;
such that when the scan head moves up and down, the laser energy emitted from the laser energy sources sweeps up and down; and
    c. an adjustor that, during treatment, changes the amplitude of the sweep.

2. The laser device of claim 1 wherein one or more of the laser energy sources emits laser energy in the red range.

3. The laser device of claim 1 wherein the scan head is connected to the body housing at a housing mount and the scan head moves in a reciprocating motion relative to the body housing by rotating about the housing mount.

4. The laser device of claim 1 wherein the laser energy emitted from at least one of the laser energy sources forms a line of laser energy where it impinges a patient's skin.

5. The laser device of claim 1 wherein the scanning mechanism further comprises a rocker and rocker motor.

6. A laser device comprising:
    a. a scan head comprising one or more laser energy sources in a scan head housing;
    b. a body housing connected to the scan head at a housing mount wherein the scan head moves relative to the body housing by rotating about an axis A of the housing mount;
    c. a scanning mechanism comprising:
       i. a rotational motor and a pushrod drive cam aligned coaxially along an axis D that is parallel to axis A;
       ii. a pushrod connected at its proximal end to the pushrod drive cam along an axis C and connected at its distal end to the scan head housing along an axis B;
such that when the rotational motor turns the pushrod drive cam, the pushrod moves the scan head up and down and causes laser energy emitted from the scan head to sweep up and down across a desired target area; and
    d. an adjustor that, during treatment, changes the amplitude of the sweep.

7. The laser device of claim 6 wherein one or more of the laser energy sources emits laser energy in the red range.

8. The laser device of claim 7 wherein the adjustor comprises:
    a. a guide bearing connected to the proximal end of the pushrod;
    b. a cam having a face and a back, wherein the face is concave and the guide bearing rides against the face; and
    c. a knob that is connected to the back of the cam wherein turning the knob in a first direction causes the face of the cam to move closer to the guide bearing and shortens the stroke length of the pushrod to decrease the amplitude of the sweep and turning the knob in a second direction causes the face of the cam to move farther away from the guide bearing and lengthens the stroke length of the pushrod to increase the amplitude of the sweep.

9. The laser device of claim 6 further comprising a spring in the pushrod drive cam that urges the pushrod to the perimeter of the cam.

10. The laser device of claim 6 wherein the laser energy emitted from at least one of the laser energy sources is a line of laser energy.

11. The laser device of claim 9 wherein the laser energy emitted from at least one of the laser energy sources is a line of laser energy.

12. The laser device of claim 9 wherein the wavelength of the laser energy emitted from at least one of the laser energy sources is in the red range.

13. The laser device of claim 9 wherein the body housing is configured to fit in an operator's hand.

14. The laser device of claim 11 wherein the body housing is configured to fit in a stationary holder.

15. A laser device comprising:
    a. a housing mount having an axis A;
    b. a scan head comprising one or more laser energy sources disposed in a scan head housing, the scan head rotatably attached to the housing mount;
    c. a body housing connected to the housing mount;
    d. a scanning mechanism disposed in the body housing comprising:
       i. a rotational motor, a pushrod drive cam, and a cam aligned coaxially along an axis D that is parallel to axis A;
       ii. a pushrod connected at its proximal end to the pushrod drive cam along an axis C that is parallel to axis A and connected at its distal end to the scan head housing along an axis B that is parallel to axis A; and
       iii. a guide bearing connected to the proximal end of the pushrod coaxially along axis C;
such that when the rotational motor turns the pushrod drive cam, the pushrod moves the scan head up and down and causes a line of laser energy to sweep up and down across a desired target area.

* * * * *